(12) United States Patent
Marnay et al.

(10) Patent No.: US 8,882,839 B2
(45) Date of Patent: *Nov. 11, 2014

(54) INTERVERTEBRAL IMPLANT

(71) Applicant: DePuy Synthes Products, LLC, Raynham, MA (US)

(72) Inventors: Thierry Marnay, Montpellier (FR); Boris Beyersdorff, Berlin (FR)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/777,076

(22) Filed: Feb. 26, 2013

(65) Prior Publication Data

US 2013/0173005 A1    Jul. 4, 2013

Related U.S. Application Data

(63) Continuation of application No. 10/998,951, filed on Nov. 30, 2004, now Pat. No. 8,506,634, which is a continuation of application No. 10/018,402, filed as application No. PCT/EP99/04628 on Jul. 2, 1999, now Pat. No. 6,936,071.

(51) Int. Cl.
*A61F 2/44* (2006.01)
*A61F 2/30* (2006.01)
*A61F 2/46* (2006.01)

(52) U.S. Cl.
CPC ....... *A61F 2/4425* (2013.01); *A61F 2220/0025* (2013.01); *A61F 2002/30383* (2013.01); *A61F*

(Continued)

(58) Field of Classification Search
CPC ........... A61F 2/4425; A61F 2220/0008; A61F 2220/0016; A61F 2002/30841; A61F 2002/30843; A61F 2002/30845; A61F 2002/30848; A61F 2002/30878; A61F 2002/30879; A61F 2002/30884; A61F 2002/30904
USPC ............................................ 623/17.11–17.16
See application file for complete search history.

(56) References Cited

U.S. PATENT DOCUMENTS

| | | | |
|---|---|---|---|
| 114,816 | A | 5/1871 | Hiestand |
| 3,320,951 | A | 5/1967 | Wittebol |

(Continued)

FOREIGN PATENT DOCUMENTS

| | | |
|---|---|---|
| CH | 624 573 | 8/1981 |
| CN | 101027005 | 8/2007 |

(Continued)

OTHER PUBLICATIONS

U.S. Appl. No. 11/185,781, filed Jul. 21, 2005, Marnay.

(Continued)

*Primary Examiner* — Thomas J Sweet
*Assistant Examiner* — Cheryl Miller
(74) *Attorney, Agent, or Firm* — Baker & Hostetler LLP

(57) ABSTRACT

In an intervertebral implant, having an upper part that has a support face for a vertebra and a lower part that has a support face for an adjacent vertebra, on each of which parts engagement elements, which are accessible from one side of the intervertebral implant, for a manipulation instrument are disposed, in order to minimize the structural height of the intervertebral implant upon insertion into an intervertebral space, it is proposed that the upper part and lower part each have protrusions and recesses aimed at the respectively other part, which are offset laterally from one another in such a way that when the upper part has been brought close to the lower part they mesh with one another; and that the engagement elements on the upper part and on the lower part are each disposed in protrusions of these parts in such a way that the engagement elements of the upper part and lower part are located side by side and at least partly overlap in the direction of the height of the intervertebral implant.

18 Claims, 4 Drawing Sheets

(52) U.S. Cl.
CPC .......... 2250/0036 (2013.01); *A61F 2002/30504* (2013.01); *A61F 2230/0013* (2013.01); *A61F 2002/30904* (2013.01); *A61F 2002/30848* (2013.01); *A61F 2230/0017* (2013.01); *A61F 2/442* (2013.01); *A61F 2002/30138* (2013.01); *A61F 2310/00023* (2013.01); *A61F 2002/30604* (2013.01); *A61F 2/30767* (2013.01); *A61F 17/025* (2013.01); *A61F 2002/30324* (2013.01); *A61F 2002/30662* (2013.01); *A61F 2/4611* (2013.01); *A61F 2002/30892* (2013.01); *A61F 2002/443* (2013.01); *A61F 2002/30884* (2013.01); *A61F 2002/30131* (2013.01); *A61F 2002/30808* (2013.01)
USPC ..................................................... 623/17.15

(56) References Cited

U.S. PATENT DOCUMENTS

| | | | |
|---|---|---|---|
| 3,486,505 A | 12/1969 | Morrison | |
| 3,510,883 A | 5/1970 | Catchcart | |
| 3,579,829 A | 5/1971 | Sampson | |
| 3,740,769 A | 6/1973 | Haboush | |
| 3,875,595 A | 4/1975 | Froning | |
| 3,903,549 A | 9/1975 | Deyerle | |
| 3,992,726 A * | 11/1976 | Freeman et al. | 623/23.4 |
| D243,286 S | 2/1977 | Deyerle | |
| 4,021,864 A | 5/1977 | Waugh | |
| 4,034,746 A | 7/1977 | Williams | |
| 4,038,897 A | 8/1977 | Murray et al. | |
| 4,038,987 A | 8/1977 | Komiya | |
| 4,232,404 A | 11/1980 | Samuelson et al. | |
| 4,309,777 A | 1/1982 | Patil | |
| 4,349,921 A | 9/1982 | Kuntz | |
| 4,467,802 A | 8/1984 | Maslanka | |
| 4,470,158 A | 9/1984 | Pappas et al. | |
| 4,545,374 A | 10/1985 | Jacobson | |
| 4,550,450 A | 11/1985 | Kinnett | |
| 4,622,959 A | 11/1986 | Marcus | |
| 4,653,487 A | 3/1987 | Maale | |
| 4,681,589 A | 7/1987 | Tronzo | |
| 4,697,586 A | 10/1987 | Gazale | |
| 4,714,469 A | 12/1987 | Kenna | |
| 4,736,738 A | 4/1988 | Lipovsek et al. | |
| 4,743,262 A | 5/1988 | Tronzo | |
| 4,759,766 A | 7/1988 | Buettner-Janz et al. | |
| 4,759,769 A | 7/1988 | Hedman et al. | |
| 4,770,661 A | 9/1988 | Oh | |
| 4,805,607 A | 2/1989 | Engelhardt et al. | |
| 4,863,476 A | 9/1989 | Shepperd | |
| 4,874,389 A | 10/1989 | Downey | |
| 4,875,474 A | 10/1989 | Border | |
| 4,892,545 A | 1/1990 | Day et al. | |
| 4,932,975 A | 6/1990 | Main et al. | |
| 4,936,853 A | 6/1990 | Fabian et al. | |
| 4,936,863 A | 6/1990 | Hofmann | |
| 4,946,378 A | 8/1990 | Hirayama et al. | |
| 4,997,432 A | 3/1991 | Keller | |
| 5,002,576 A | 3/1991 | Fuhrmann et al. | |
| 5,004,476 A | 4/1991 | Cook | |
| 5,022,576 A | 6/1991 | Jenq | |
| 5,035,716 A * | 7/1991 | Downey | 623/17.16 |
| 5,037,438 A | 8/1991 | Davidson | |
| 5,062,850 A | 11/1991 | MacMillan et al. | |
| 5,071,437 A | 12/1991 | Steffee | |
| 5,108,442 A | 4/1992 | Smith | |
| 5,122,130 A | 6/1992 | Keller | |
| 5,171,280 A | 12/1992 | Baumgartner | |
| 5,192,327 A | 3/1993 | Brantigan | |
| 5,211,645 A | 5/1993 | Baumgart et al. | |
| 5,228,455 A | 7/1993 | Barcel | |
| 5,236,460 A | 8/1993 | Barber | |
| 5,258,031 A | 11/1993 | Salib et al. | |
| 5,271,737 A | 12/1993 | Baldwin et al. | |
| 5,282,868 A | 2/1994 | Bahler | |
| 5,290,312 A | 3/1994 | Kojimoto et al. | |
| 5,306,308 A | 4/1994 | Gross et al. | |
| 5,306,309 A | 4/1994 | Wagner et al. | |
| 5,314,477 A * | 5/1994 | Marnay | 623/17.15 |
| 5,326,366 A | 7/1994 | Pascarella et al. | |
| 5,336,232 A | 8/1994 | Green et al. | |
| 5,344,458 A | 9/1994 | Bonutti | |
| 5,364,397 A | 11/1994 | Hayes et al. | |
| 5,370,697 A | 12/1994 | Baumgartner | |
| 5,383,888 A | 1/1995 | Zvenyatsky et al. | |
| 5,395,317 A | 3/1995 | Kambin | |
| 5,401,269 A | 3/1995 | Buttner-Janz et al. | |
| 5,409,492 A | 4/1995 | Jones et al. | |
| 5,423,825 A | 6/1995 | Levine | |
| 5,425,773 A | 6/1995 | Boyd et al. | |
| 5,431,658 A | 7/1995 | Moskovich | |
| 5,443,514 A | 8/1995 | Steffee | |
| 5,458,641 A | 10/1995 | Ramirez | |
| 5,484,437 A | 1/1996 | Michelson | |
| 5,489,307 A | 2/1996 | Kuslich et al. | |
| 5,501,654 A | 3/1996 | Failla et al. | |
| 5,505,732 A | 4/1996 | Michelson | |
| 5,507,816 A | 4/1996 | Bullivant | |
| 5,507,821 A | 4/1996 | Sennwald et al. | |
| 5,509,934 A | 4/1996 | Cohen | |
| 5,534,029 A | 7/1996 | Shima | |
| 5,534,030 A | 7/1996 | Navarro et al. | |
| 5,545,229 A | 8/1996 | Parsons et al. | |
| 5,554,191 A | 9/1996 | Lahille et al. | |
| 5,556,431 A | 9/1996 | Buttner-Janz et al. | |
| 5,562,736 A | 10/1996 | Ray et al. | |
| 5,562,738 A | 10/1996 | Boyd et al. | |
| 5,571,109 A | 11/1996 | Bertagnoli | |
| 5,591,235 A | 1/1997 | Kuslich | |
| 5,609,636 A | 3/1997 | Kohrs et al. | |
| 5,658,347 A | 8/1997 | Sarkisian et al. | |
| 5,674,296 A * | 10/1997 | Bryan et al. | 623/17.16 |
| 5,676,701 A | 10/1997 | Yuan et al. | |
| 5,683,465 A | 11/1997 | Shinn et al. | |
| 5,702,469 A | 12/1997 | Whipple et al. | |
| 5,702,486 A | 12/1997 | Craig et al. | |
| 5,716,415 A | 2/1998 | Steffee | |
| 5,720,751 A | 2/1998 | Jackson | |
| 5,722,977 A | 3/1998 | Wilhelmy | |
| 5,755,798 A | 5/1998 | Papavero et al. | |
| 5,755,811 A | 5/1998 | Tanamal et al. | |
| 5,776,199 A | 7/1998 | Michelson | |
| 5,782,830 A | 7/1998 | Farris | |
| 5,782,832 A | 7/1998 | Larsen et al. | |
| 5,797,909 A | 8/1998 | Michelson | |
| 5,800,547 A | 9/1998 | Schafer et al. | |
| 5,824,094 A | 10/1998 | Serhan et al. | |
| D401,335 S | 11/1998 | Koros et al. | |
| 5,865,848 A | 2/1999 | Baker | |
| 5,885,300 A | 3/1999 | Tokuhashi et al. | |
| 5,888,226 A | 3/1999 | Rogozinski | |
| 5,895,428 A | 4/1999 | Berry | |
| 5,897,593 A | 4/1999 | Kohrs et al. | |
| 5,899,901 A | 5/1999 | Middleton | |
| 5,899,941 A | 5/1999 | Nishijima et al. | |
| 5,951,564 A | 9/1999 | Schroder et al. | |
| 6,006,174 A | 12/1999 | Lin et al. | |
| 6,010,502 A * | 1/2000 | Bagby | 606/247 |
| 6,017,342 A | 1/2000 | Rinner | |
| 6,033,405 A | 3/2000 | Winslow et al. | |
| 6,036,692 A | 3/2000 | Burel et al. | |
| 6,039,763 A | 3/2000 | Shelokov | |
| 6,042,582 A | 3/2000 | Ray | |
| 6,059,790 A | 5/2000 | Sand et al. | |
| 6,063,088 A | 5/2000 | Winslow | |
| 6,063,121 A * | 5/2000 | Xavier et al. | 623/17.15 |
| 6,080,155 A | 6/2000 | Michelson | |
| 6,083,225 A | 7/2000 | Winslow et al. | |
| 6,086,595 A | 7/2000 | Yonemura et al. | |
| 6,096,038 A | 8/2000 | Michelson | |
| 6,096,080 A | 8/2000 | Nicholson et al. | |
| 6,102,950 A | 8/2000 | Vaccaro | |
| 6,102,954 A | 8/2000 | Albrektsson et al. | |
| 6,110,179 A | 8/2000 | Flivik et al. | |

(56) References Cited

U.S. PATENT DOCUMENTS

| | | | |
|---|---|---|---|
| 6,113,602 A | 9/2000 | Sand | |
| 6,113,637 A | 9/2000 | Gill et al. | |
| 6,113,638 A | 9/2000 | Williams et al. | |
| 6,126,660 A | 10/2000 | Dietz | |
| 6,126,674 A | 10/2000 | Janzen | |
| 6,146,421 A * | 11/2000 | Gordon et al. | 623/17.15 |
| 6,156,040 A | 12/2000 | Yonemura et al. | |
| 6,159,215 A | 12/2000 | Urbahns et al. | |
| 6,171,339 B1 | 1/2001 | Houfburg et al. | |
| 6,174,311 B1 | 1/2001 | Branch et al. | |
| 6,179,874 B1 | 1/2001 | Cauthen | |
| 6,224,599 B1 | 5/2001 | Baynham et al. | |
| 6,238,414 B1 | 5/2001 | Griffiths | |
| 6,241,769 B1 | 6/2001 | Nicholson et al. | |
| 6,251,140 B1 | 6/2001 | Marino et al. | |
| 6,261,296 B1 | 7/2001 | Aebi et al. | |
| 6,264,655 B1 | 7/2001 | Pisharodi | |
| 6,270,498 B1 | 8/2001 | Michelson | |
| 6,296,647 B1 | 10/2001 | Robioneck et al. | |
| 6,309,421 B1 | 10/2001 | Pisharodi | |
| 6,368,350 B1 * | 4/2002 | Erickson et al. | 623/17.14 |
| 6,368,351 B1 | 4/2002 | Glenn et al. | |
| 6,368,353 B1 | 4/2002 | Arcand | |
| 6,375,681 B1 | 4/2002 | Truscott | |
| 6,395,030 B1 | 5/2002 | Songer et al. | |
| 6,402,785 B1 | 6/2002 | Zdeblick et al. | |
| 6,413,278 B1 | 7/2002 | Marchosky | |
| 6,436,139 B1 | 8/2002 | Shapiro et al. | |
| 6,440,142 B1 | 8/2002 | Ralph et al. | |
| 6,440,168 B1 | 8/2002 | Cauthen | |
| 6,440,169 B1 | 8/2002 | Elberg et al. | |
| 6,447,547 B1 | 9/2002 | Michelson | |
| 6,478,800 B1 | 11/2002 | Fraser et al. | |
| 6,478,801 B1 | 11/2002 | Ralph et al. | |
| 6,478,823 B1 | 11/2002 | Michelson | |
| 6,500,206 B1 | 12/2002 | Bryan | |
| 6,517,544 B1 | 2/2003 | Michelson | |
| 6,558,424 B2 | 5/2003 | Thalgott | |
| 6,565,574 B2 | 5/2003 | Michelson | |
| 6,595,995 B2 | 7/2003 | Zdeblick et al. | |
| 6,599,294 B2 | 7/2003 | Fuss et al. | |
| 6,610,065 B1 | 8/2003 | Branch et al. | |
| 6,613,091 B1 | 9/2003 | Zdeblick et al. | |
| 6,626,943 B2 | 9/2003 | Eberlein et al. | |
| 6,635,060 B2 | 10/2003 | Hanson et al. | |
| 6,641,582 B1 | 11/2003 | Hanson et al. | |
| 6,641,614 B1 | 11/2003 | Wagner et al. | |
| 6,652,533 B2 | 11/2003 | O'Neil | |
| 6,652,534 B2 | 11/2003 | Zucherman et al. | |
| 6,679,886 B2 | 1/2004 | Weikel et al. | |
| 6,712,819 B2 | 3/2004 | Zucherman et al. | |
| 6,712,825 B2 | 3/2004 | Aebi et al. | |
| 6,733,505 B2 | 5/2004 | Li | |
| 6,740,118 B2 * | 5/2004 | Eisermann et al. | 623/17.14 |
| 6,746,454 B2 | 6/2004 | Winterbottom et al. | |
| 6,755,841 B2 | 6/2004 | Fraser et al. | |
| 6,770,074 B2 | 8/2004 | Michelson | |
| 6,824,565 B2 | 11/2004 | Muhanna et al. | |
| 6,835,207 B2 * | 12/2004 | Zacouto et al. | 623/17.12 |
| 6,875,213 B2 | 4/2005 | Michelson | |
| 6,896,676 B2 | 5/2005 | Zubok et al. | |
| 6,936,071 B1 * | 8/2005 | Marnay et al. | 623/17.15 |
| 6,964,687 B1 | 11/2005 | Bernard et al. | |
| 6,966,912 B2 | 11/2005 | Michelson | |
| 7,037,340 B2 | 5/2006 | Gau | |
| 7,048,766 B2 | 5/2006 | Ferree | |
| 7,081,120 B2 | 7/2006 | Li et al. | |
| 7,083,649 B2 | 8/2006 | Zucherman et al. | |
| 7,118,580 B1 | 10/2006 | Beyersdorff et al. | |
| 7,153,303 B2 | 12/2006 | Squires et al. | |
| 7,169,182 B2 | 1/2007 | Errico et al. | |
| 7,204,852 B2 | 4/2007 | Marnay et al. | |
| 7,238,203 B2 | 7/2007 | Bagga et al. | |
| 7,252,673 B2 | 8/2007 | Lim | |
| 7,491,204 B2 | 2/2009 | Marnay | |
| 7,547,309 B2 | 6/2009 | Bertagnoli et al. | |
| 7,575,576 B2 | 8/2009 | Zubok et al. | |
| 7,641,692 B2 | 1/2010 | Bryan et al. | |
| 7,803,162 B2 | 9/2010 | Marnay et al. | |
| 7,811,325 B2 | 10/2010 | Cannon et al. | |
| 7,837,732 B2 | 11/2010 | Zucherman et al. | |
| 7,857,856 B2 | 12/2010 | Trieu | |
| 8,025,684 B2 | 9/2011 | Garcia-Bengochea et al. | |
| 8,092,542 B2 | 1/2012 | Bryan et al. | |
| 2002/0016633 A1 | 2/2002 | Lin et al. | |
| 2002/0049497 A1 | 4/2002 | Mason | |
| 2002/0065558 A1 | 5/2002 | Varga et al. | |
| 2002/0072752 A1 | 6/2002 | Zucherman et al. | |
| 2002/0077702 A1 | 6/2002 | Castro | |
| 2002/0165612 A1 | 11/2002 | Gerber et al. | |
| 2003/0028197 A1 | 2/2003 | Hanson et al. | |
| 2003/0083747 A1 | 5/2003 | Winterbottom et al. | |
| 2003/0135275 A1 | 7/2003 | Garcia et al. | |
| 2003/0191534 A1 | 10/2003 | Viart et al. | |
| 2003/0195631 A1 | 10/2003 | Ferree | |
| 2003/0208273 A1 | 11/2003 | Eisermann et al. | |
| 2003/0233145 A1 | 12/2003 | Landry et al. | |
| 2004/0002758 A1 | 1/2004 | Landry et al. | |
| 2004/0002761 A1 | 1/2004 | Rogers et al. | |
| 2004/0010316 A1 | 1/2004 | William et al. | |
| 2004/0024462 A1 | 2/2004 | Ferree et al. | |
| 2004/0030387 A1 | 2/2004 | Landry et al. | |
| 2004/0097929 A1 | 5/2004 | Branch et al. | |
| 2004/0117022 A1 | 6/2004 | Marnay et al. | |
| 2004/0133278 A1 | 7/2004 | Marino et al. | |
| 2004/0138750 A1 | 7/2004 | Mitchell | |
| 2004/0143332 A1 | 7/2004 | Krueger et al. | |
| 2004/0172133 A1 | 9/2004 | Gerber et al. | |
| 2004/0215198 A1 | 10/2004 | Marnay et al. | |
| 2004/0225295 A1 | 11/2004 | Zubok et al. | |
| 2004/0225366 A1 | 11/2004 | Eisermann et al. | |
| 2005/0021042 A1 | 1/2005 | Marnay et al. | |
| 2005/0021145 A1 | 1/2005 | de Villiers et al. | |
| 2005/0021146 A1 | 1/2005 | de Villiers et al. | |
| 2005/0043802 A1 | 2/2005 | Eisermann et al. | |
| 2005/0060034 A1 | 3/2005 | Berry et al. | |
| 2005/0060035 A1 | 3/2005 | Errico et al. | |
| 2005/0085917 A1 | 4/2005 | Marnay et al. | |
| 2005/0113926 A1 | 5/2005 | Zucherman et al. | |
| 2005/0125061 A1 | 6/2005 | Zucherman et al. | |
| 2005/0143747 A1 | 6/2005 | Zubok et al. | |
| 2005/0143749 A1 | 6/2005 | Zalenski et al. | |
| 2005/0143820 A1 | 6/2005 | Zucherman et al. | |
| 2005/0154462 A1 | 7/2005 | Zucherman et al. | |
| 2005/0159818 A1 | 7/2005 | Blain | |
| 2005/0165408 A1 | 7/2005 | Puno et al. | |
| 2005/0203626 A1 | 9/2005 | Sears et al. | |
| 2005/0228500 A1 | 10/2005 | Kim et al. | |
| 2005/0246022 A1 | 11/2005 | Zubok et al. | |
| 2005/0251260 A1 | 11/2005 | Gerber et al. | |
| 2005/0261769 A1 | 11/2005 | Moskowitz et al. | |
| 2005/0267581 A1 | 12/2005 | Marnay et al. | |
| 2006/0030856 A1 | 2/2006 | Drewry et al. | |
| 2006/0030860 A1 | 2/2006 | Peterman | |
| 2006/0036326 A1 | 2/2006 | Baumgartner et al. | |
| 2006/0041313 A1 | 2/2006 | Allard et al. | |
| 2006/0064100 A1 | 3/2006 | Bertagnoli et al. | |
| 2006/0074489 A1 | 4/2006 | Bryan | |
| 2006/0089656 A1 | 4/2006 | Allard et al. | |
| 2006/0100633 A1 | 5/2006 | Michelson | |
| 2006/0116769 A1 | 6/2006 | Marnay et al. | |
| 2006/0149273 A1 | 7/2006 | Ross et al. | |
| 2006/0149378 A1 | 7/2006 | Chase et al. | |
| 2006/0210594 A1 | 9/2006 | Trieu | |
| 2006/0217809 A1 | 9/2006 | Albert et al. | |
| 2006/0235533 A1 | 10/2006 | Blain | |
| 2006/0241641 A1 | 10/2006 | Albans et al. | |
| 2006/0259147 A1 | 11/2006 | Krishna et al. | |
| 2006/0265077 A1 | 11/2006 | Zwirkoski | |
| 2007/0162134 A1 | 7/2007 | Marnay | |
| 2007/0179615 A1 | 8/2007 | Heinz et al. | |
| 2007/0191955 A1 | 8/2007 | Zucherman et al. | |
| 2007/0198089 A1 | 8/2007 | Moskowitz et al. | |
| 2007/0198093 A1 | 8/2007 | Brodke et al. | |

(56) References Cited

U.S. PATENT DOCUMENTS

| | | | |
|---|---|---|---|
| 2007/0213821 A1 | 9/2007 | Kwak et al. |
| 2007/0225812 A1 | 9/2007 | Gill |
| 2007/0265707 A1 | 11/2007 | Marnay et al. |
| 2008/0133013 A1 | 6/2008 | Duggal et al. |
| 2008/0140204 A1 | 6/2008 | Heinz |
| 2008/0140208 A1 | 6/2008 | Zucherman et al. |
| 2008/0161923 A1 | 7/2008 | Parsons |
| 2008/0215156 A1 | 9/2008 | Duggal et al. |
| 2008/0228275 A1 | 9/2008 | Cannon et al. |
| 2009/0043392 A1 | 2/2009 | Duggal et al. |
| 2009/0043393 A1 | 2/2009 | Duggal et al. |
| 2009/0069894 A1 | 3/2009 | Duggal et al. |
| 2009/0076608 A1 | 3/2009 | Gordon et al. |
| 2010/0070042 A1 | 3/2010 | Bryan et al. |
| 2010/0217395 A1 | 8/2010 | Bertagnoli et al. |
| 2010/0228351 A1 | 9/2010 | Ankney et al. |
| 2010/0234954 A1 | 9/2010 | Justis et al. |
| 2010/0280617 A1 | 11/2010 | Coppes et al. |
| 2010/0292800 A1 | 11/2010 | Zubok |
| 2010/0298941 A1 | 11/2010 | Hes et al. |
| 2010/0324690 A1 | 12/2010 | Cannon et al. |
| 2011/0082556 A1 | 4/2011 | Duggal et al. |
| 2011/0087331 A1 | 4/2011 | Reichen et al. |
| 2011/0118845 A1 | 5/2011 | Overes et al. |
| 2011/0172773 A1 | 7/2011 | Reichen et al. |
| 2011/0282458 A1 | 11/2011 | Aferzon et al. |
| 2011/0295374 A1 | 12/2011 | Bryan et al. |
| 2011/0320001 A1 | 12/2011 | Hughes et al. |
| 2011/0320003 A1 | 12/2011 | Duggal et al. |
| 2012/0083888 A1 | 4/2012 | Moumene et al. |
| 2012/0101579 A1 | 4/2012 | De Villiers et al. |
| 2012/0101582 A1 | 4/2012 | Raiszadeh et al. |
| 2012/0232663 A1 | 9/2012 | Zipnick |
| 2012/0290093 A1 | 11/2012 | Hansell et al. |
| 2012/0310349 A1 | 12/2012 | Gordon et al. |
| 2012/0316648 A1 | 12/2012 | Lambrecht et al. |
| 2013/0023990 A1 | 1/2013 | Zipnick et al. |
| 2013/0110240 A1 | 5/2013 | Hansell et al. |
| 2013/0138217 A1 | 5/2013 | Laurence et al. |

FOREIGN PATENT DOCUMENTS

| | | |
|---|---|---|
| CN | 101631517 | 1/2010 |
| DE | 2263842 | 7/1974 |
| DE | 2804936 | 8/1979 |
| DE | 3023353 | 4/1981 |
| DE | 3526742 A1 | 1/1987 |
| DE | 4328690 B4 | 3/1995 |
| EP | 0077159 A1 | 4/1983 |
| EP | 0471821 B1 | 2/1992 |
| EP | 0333990 | 7/1993 |
| EP | 0770367 | 5/1997 |
| EP | 0712607 B1 | 2/2002 |
| EP | 1793749 | 6/2007 |
| EP | 2120799 | 11/2009 |
| FR | 2718635 | 10/1995 |
| FR | 2724108 | 3/1996 |
| FR | 2737656 | 2/1997 |
| FR | 2742653 | 6/1997 |
| FR | 2795945 A1 | 1/2001 |
| JP | 2-261446 | 10/1990 |
| JP | 2010-521244 | 6/2010 |
| WO | WO 91/13598 A1 | 9/1991 |
| WO | WO 98/34552 A1 | 8/1998 |
| WO | WO 01/01893 | 1/2001 |
| WO | WO 01/19295 A1 | 3/2001 |
| WO | WO 02/071986 A2 | 9/2002 |
| WO | WO 03/053290 A1 | 7/2003 |
| WO | WO 2004/019828 | 3/2004 |
| WO | WO 2004/098380 | 11/2004 |
| WO | WO 2005/051243 | 6/2005 |
| WO | WO 2005/053580 | 6/2005 |
| WO | WO 2006/033067 | 3/2006 |
| WO | WO 2006/036580 | 4/2006 |
| WO | WO 2008/014258 | 1/2008 |
| WO | WO 2008/112956 | 9/2008 |
| ZA | 2009/05900 | 5/2010 |

OTHER PUBLICATIONS

"A New Tibia Plateau", The Journal of Bone and Joint Surgery, Jul. 1970, 52-A(5), 2 pages.

"Amended Answer and Counterclaims", In the United States District Court, Western District of Tennessee, Case No. 2:07-cv-02175-JPM-dkv, dated Nov. 21, 2007, 187 pages.

"Amended Judgment Awarding Enhanced Damages, Prejudgment Interest and Attorney Fees" (Filed Nov. 9, 2009, Doc. 521), 2 pages.

"Amended Order Denying Defendants' Motion for Summary Judgment of Invalidity Under 35 U.S.C. § 103" (Dated Nov. 6, 2008, Doc. 332), 20 pages.

"Amended Order Denying Medtronic's Renewed Motion for Judgment as a Matter of Law and Alternative Motion for a New Trial" (Filed Aug. 20, 2009, doc. 494), 30 pages.

"Answer and Counterclaims", In the United States District Court, Western District of Tennessee, Case No. 2:07-cv-02175-JPM-dkv, filed May 4, 2007, 6 pages.

"Answers and Counterclaims", In the United States District Court, Western District of Tennessee, Case No. 2:07-cv-02175-JPM-dkv, filed May 4, 2007, 6 pages.

"Appeal from the US District Court: *Spine Solutions, Inc.* vs. *Medtronic Sofamor Danek USA, Inc.*", In the United States Court for the Western District of Tennessee, Case No. 07-CV-02175, Decided: Sep. 9, 2010, 28 pages.

"Brief in Support of Medtronic's Motion for Judgment as a Matter of Law on the Obviousness of the '071 Patent, No Willful Infringement and No Lost Profits", In the United States District Court, Western District of Tennessee, Case No. 2:07-cv-02175-JPM, filed Dec. 4, 2008, 9 pages.

"Citation of Supplemental Authority in Support of Medtronic's Renewed Motion for Judgment as a Matter of Law and Alternative Motion for a New Trial", In the United States District Court, Western District of Tennessee, Case No. 2:07-cv-02175-JPM-dkv, filed Feb. 18, 2009, 4 pages.

"Civil Docket sheet", In the United States District Court, Western District of Tennessee, Case No. 2:07-cv-02175-JPM-dkv, filed Mar. 7, 2007, 36 pages.

"Defendant's Medtronic Sofamor Danek, Inc. and Medtronic Sofamor Danek USA, Inc.'s Third Supplemental Answers and Objections to Plaintiff's First Set of Interrogatories Nos. 1-6", In the United States District Court, Western District of Tennessee, Case No. 2:07-cv02175-JPM-dkv, dated Oct. 15, 2007, 57 pages.

"Defendant's Supplemental Brief in Support of Their Motions for Summary Judgment of Invalidity Under 35 U.S.C. section 103", In the United States District Court, Western District of Tennessee, Case No. 2:07-cv-02175-JPM-dkv, filed Jun. 19, 2008, 4 pages.

"Defendants Medtronic Sofamor Danek, Inc. and Medtronic Sofamor Danek USA, Inc.'s Sixth Supplemental Answers and Objections to Plaintiff's First Set of Interrogatories", In the United States District Court, Western District of Tennessee, Case No. 2:07-cv-02175-JPM-dkv, filed Dec. 14, 2007, 40 pages.

"Defendants' Opening Markman Brief", In the United States District Court, Western District of Tennessee, Case No. 2:07-cv-02175-JPM-dkv, filed Feb. 19, 2008, 29 pages.

"Defendants' Reply Markman Brief", In the United States District Court, Western District of Tennessee, Case No. 2:07-cv-02175-JPM-dkv, filed Mar. 31, 2008, 21 pages.

"Defendants' Responsive Markman Brief", In the United States District Court, Western District of Tennessee, Case No. 2:07-cv-02175-JPM-dkv, filed Mar. 17, 2008, 26 pages.

"Expert Report #2 Rebuttal to Other Reports in this Litigation", In the United States District Court, Western District of Tennessee, Case No. 2:07-cv-02175-JPM-dkv, filed Dec. 21, 2007, 36 pages.

"Expert Report of Charles A. Laff", In the United States District Court, Western District of Tennessee, Case No. 2:07-cv-02175-JPM-dkv, filed Feb. 19, 2008, 168 pages.

(56) References Cited

OTHER PUBLICATIONS

"Expert Report of Dr. Thomas A. Zdeblick, M.D.", In the United States District Court, Western District of Tennessee, Case No. 2:07-cv-02175-JPM-dkv, filed Nov. 21, 2007, 77 pages.
"Expert Report of Mark E. Nusbaum", In the United States District Court, Western District of Tennessee, Case No. 2:07-cv-02175-JPM-dkv, filed Dec. 21, 2007, 51 pages.
"Expert Report of Stephen D. Cook, Ph.D.", In the United States District Court, Western District of Tennessee, Case No. 2:07-cv-02175-JPM-dkv, dated Nov. 21, 2007, 200 pages.
"Here's a Good Skate", The Journal of Bone and Joint Surgery, Sep. 1971, 53-A(6), 2 pages.
"Judgment Awarding Enhanced Damages, Post-Dec. 31, 2007 Damages, Pre- and Post-Judgment Interest, and Injunctive Relief" (Filed Aug. 26, 2009, Doc. 497), 2 pages.
"Judgment", In the United States District Court, Western District of Tennessee, Case No. 2:07-cv-02175-JPM-dkv, filed Dec. 8, 2008, 2 pages.
"Jury Verdict Form", In the United States District Court, Western District of Tennessee, Case No. 2:07-cv-02175-JPM-dkv, filed Dec. 5, 2008, 4 pages.
"Memorandum in Support of Medtronic's Renewed Motion for Judgment as a Matter of Law and Alternative Motion for a New Trial", In the United States District Court, Western District of Tennessee, Case No. 2:07-cv-02175-JPM-dkv, filed Dec. 22, 2008, 614 pages.
"Memorandum in Support of Plaintiffs' Motion for Judgment as a Matter of Law that the '071 Patent Is Not Invalid for Obviousness", In the United States District Court, Western District of Tennessee, Case No. 2:07-cv-02175-JPM-dkv, filed Dec. 4, 2008, 5 pages.
"Order Amending and Altering the Judgment Entered on Aug. 26, 2009 to Alter the Amount of Damages and Interest Awarded and to Amend the Judgment to Provide for an Award of Attorney Fees" (Filed Nov. 9, 2009, Doc. 520), 20 pages.
"Order Denying Defendants' Motion for Summary Judgment of Invalidity under 35 U.S.C. § 103" (Dated Sep. 30, 2008, Doc. 317), 20 pages.
"Order Denying Defendants' Motion for Summary Judgment of No Willful Infringement" (Dated Sep. 30, 2008, Doc. 318), 12 pages.
"Order Denying Defendants' Motion for Summary Judgment of Non-infringement on O-MAV; Order Granting Plaintiff Spine Solutions, Inc.'s Motion for Partial Summary Judgment of Infringement of Claims 1 and 2 of U.S. Patent No. 6,939,071" (Dated Sep. 30, 2008, Doc. 313), 14 pages.
"Order Denying Defendants' Motion for Summary Judgment of Non-infringement, or in the Alternative for Invalidity; Order Granting Plaintiff Spine Solutions, Inc.'s Motion for Partial Summary Judgment Dismissing Medtronic's 35 U.S.C. § 112 Defenses" (Dated Sep. 30, 2008, Doc. 314), 16 pages.
"Order Denying Plaintiff Spine Solutions, Inc.'s Motion for Summary Judgment Regarding the Obviousness Defense", filed Nov. 6, 2008, 2 pages.
"Order Denying Plaintiffs' Motion to Unseal the Court's Summary Judgment Orders, Post-Trial Orders, and Judgments" (Filed Dec. 23, 2009, doc. 525), 8 pages.
"Order Following Markman Hearing", In the United States District Court, Western District of Tennessee, Case No. 2:07-cv-02175-JPM-dkv, filed Jul. 2, 2008, 36 pages.
"Order Granting in Part and Denying in Part Plaintiffs' Motion for Treble Damages, Award of Attorney Fees, Expert Witness Fees, Expenses, Post Dec. 31, 2007 damages, and Pre- and Post-Judgment Interest" (Filed Aug. 26, 2009, Doc. 495), 24 pages.
"Order Granting Plaintiff Spine Solutions, Inc.'s Motion for Partial Summary Judgment (1) that the Asserted Claims of the '071 Patent are Not Anticipated; and (2) that the (a) '785 Patent [No. 6,402,785], (b) Dr. Zdeblick and Mr. McKay's Alleged Invention, and (c) Numerous Unexplained References are Not Prior Art" (Dated Sep. 30, 2008, Doc. 315), 14 pages.
"Order Granting Plaintiff Spine Solutions, Inc.'s Motion for Partial Summary Judgment of Failure of Defendants to State a Legal Defense or Claim for Relief Based on Inequitable Conduct" (Dated Sep. 30, 2008, Doc. 316), 10 pages.
"Order Granting Plaintiffs' Motion for Permanent Injunction" (Filed Aug. 26, 2009, doc. 496), 24 pages.
"Plaintiff Spine Solutions Inc.'s Memorandum of Facts and Law in Support of its Response to Defendants' Motion to Amend their Answer to Allege Inequitable Conduct", In the United States District Court, Western District of Tennessee, Case No. 2:07-cv-02175-JPM-dkv, filed Dec. 7, 2007, 23 pages.
"Plaintiff Spine Solutions Inc.'s Motion for Leave to File a Surreply to Defendants' Reply Markman Brief", In the United States District Court, Western District of Tennessee, Case No. 2:07-cv-02175-JPM-dkv, filed Apr. 7, 2008, 2 pages.
"Plaintiff Spine Solutions Inc.'s Reply Markman Brief", In the United States District Court, Western District of Tennessee, Case No. 2:07-cv-02175-JPM-dkv, filed Mar. 31, 2008, 24 pages.
"Plaintiff Spine Solutions Inc.'s Response to Defendants' Motion to Amend their Answer to Allege Inequitable Conduct", In the United States District Court, Western District of Tennessee, Case No. 2:07-cv-02175-JPM-dkv, filed Dec. 7, 2007, 2 pages.
"Plaintiff Spine Solutions' Responsive Markman Brief", In the United States District Court, Western District of Tennessee, Case No. 2:07-cv-02175-JPM-dkv, filed Mar. 17, 2008, 25 pages.
"Plaintiff's Supplemental Response to Defendants' Interrogatory No. 2 (relating to Conception Reduction to Practice, First Sale)" In the United States District Court, Western District of Tennessee, Case No. 2:07-cv-02175-JPM-dkv, filed Oct. 29, 2007, 8 pages.
"Plaintiffs' Memorandum in Opposition to Medtronic's Renewed Motion for Judgment as a Matter of Law and Alternative Motion for a New Trial", In the United States District Court, Western District of Tennessee, Case No. 2:07-cv-02175-JPM-dkv, filed Jan. 23, 2009, 40 pages.
"Plaintiffs' Memorandum in Response to Medtronic's Reply Memorandum and Citation of Supplemental Authority, Regarding Medtronic's Renewed Motion for Judgment as a Matter of Law and Alternative Motion for a New Trial", In the United States District Court, Western District of Tennessee, Case No. 2:07-cv-02175-JPM-dkv, filed Mar. 11, 2009.
"Plaintiffs' Motion and Supporting Memorandum to Unseal the Court's Post-Trial Orders, Judgments, and Summary Judgment Orders" (Filed Nov. 17, 2009, doc. 523), 7 pages.
"Rebuttal Expert Report of Mark E. Nusbaum", In the United States District Court, Western District of Tennessee, Case No. 2:07-cv-02175-JPM-dkv, filed Dec. 21, 2007, 51 pages.
"Reply Brief in Support of Plaintiff Spine Solutions Inc.'s Motion for Partial Summary Judgment Dismissing Medtronic's 35 U.S.C. section 112 Defenses", In the United States District Court, Western District of Tennessee, Case No. 2:07-cv-02175-JPM-dkv, filed Mar. 31, 2008, 24 pages.
"Reply Memorandum in Support of Medtronic's Renewed Motion for Judgment as a Matter of Law and Alternative Motion for a New Trial", In the United States District Court, Western District of Tennessee, Case No. 2:07-cv-02175-JPM-dkv, filed Feb. 10, 2009, 26 pages.
"Transcript of Trial Proceedings: Testimony of Dr. Thierry Marnay, Part 1", In the United States District Court, Western District of Tennessee, Case No. 2:07-cv-02175-JPM-dkv, Nov. 25-26, 2008, 334 pages.
"Transcript of Trial Proceedings" In the United States District Court, Western District of Tennessee, Case No. 2:07-cv-02175-JPM-dkv, Dec. 3, 2008, 246 pages.
"Transcript of Trial Proceedings", In the United States District Court, Western District of Tennessee, Case No. 2:07-cv-02175-JPM-dkv, Dec. 1-2, 2008, 192 pages.
"Transcript of Trial Proceedings", In the United States District Court, Western District of Tennessee, Case No. 2:07-cv-02175-JPM-dkv, Dec. 4, 2008, 103 pages.
Ahrens et al., "Normal Joint Mobility is Maintained with an Artificial Disc Prosthesis", Waldemar Link, 1996, 4 pages.
English Abstract, DE 3526742 A1, Jansson, Jan. 29, 1987.
European Patent Application No. EP 05795413: European Search Report dated Aug. 10, 2011, 7 pages.

(56) References Cited

OTHER PUBLICATIONS

Hoogland et al., "Total Lumbar Intervertebral Disc Replacement: Testing of a New Articulating Spacer in Human Cadaver Spines", 24th Annual ORS, Feb. 21-23, 1978, 1 page.

In the United States Patent and Trademark Office, "Notice of Intent to Issue Ex Parte Reexamination Certificate," Ex Parte Reexamination No. 90/010,655 and No. 90/009,542, Filed Aug. 24, 2009 and Jul. 24, 2009, date mailed Jul. 14, 2010, 9 pages.

In the United States Patent and Trademark Office, "Patent Owner's Response Pursuant to 37 C.F.R. § 1.550 in Merged Ex Parte Reexamination of U.S. Patent No. 6,936,071," Ex Parte Reexamination No. 90/010,655 and No. 90/009,542, Filed Aug. 24, 2009 and Jul. 24, 2009, dated May 19, 2010, 36 pages.

In the United States Patent and Trademark Office, "Request for Ex Parte Reexamination", In re patent of: Marnay et al., U.S. patent # 6,936,071, filed on Jul. 24, 2009, 70 pages.

In the United States Patent and Trademark Office, "Request for Ex Parte Reexamination", In re patent of: Marnay et al., U.S. patent # 6,936,071, filed on Aug. 24, 2009, 23 pages.

In the United States Patent and Trademark Office, in Re. U.S. Appl. No. 10/070,823, filed Jul. 15, 2002 Notice of Allowance mailed Jul. 24, 2006.

In the United States Patent and Trademark Office, in Re. U.S. Appl. No. 10/070,823, filed Jul. 15, 2002, Examiner Interview Summary Record and Notice of Allowance mailed Jul. 13, 2006.

In the United States Patent and Trademark Office, in Re. U.S. Appl. No. 10/070,823, filed Jul. 15, 2002, Final Rejection mailed Aug. 23, 2005.

In the United States Patent and Trademark Office, in Re. U.S. Appl. No. 10/070,823, filed Jul. 15, 2002, Non-Final Office Action, mailed Sep. 23, 2004.

In the United States Patent and Trademark Office, in Re. U.S. Appl. No. 10/318,078, filed Dec. 13, 2002, Issue Notice mailed Mar. 28, 2007.

In the United States Patent and Trademark Office, in Re. U.S. Appl. No. 10/318,078, filed Dec. 13, 2002, Notice of Allowance mailed Feb. 26, 2007.

In the United States Patent and Trademark Office, in Re. U.S. Appl. No. 10/318,078, filed Dec. 13, 2002, Final Rejection mailed Aug. 1, 2006.

In the United States Patent and Trademark Office, in Re. U.S. Appl. No. 10/318,078, filed Dec. 13, 2002, Final Rejection mailed Nov. 12, 2004.

In the United States Patent and Trademark Office, in Re. U.S. Appl. No. 10/318,078, filed Dec. 13, 2002, Non-Final Office Action mailed Apr. 21, 2004.

In the United States Patent and Trademark Office, in Re. U.S. Appl. No. 10/318,078, filed Dec. 13, 2002, Non-Final Office Action mailed Aug. 8, 2005.

In the United States Patent and Trademark Office, in Re. U.S. Appl. No. 10/622,535, filed Jul. 21, 2003: Non Final Office Action mailed Apr. 26, 2007.

In the United States Patent and Trademark Office, in Re. U.S. Appl. No. 10/622,535, filed Jul. 21, 2003: Non Final Office Action mailed Aug. 30, 2005.

In the United States Patent and Trademark Office, in Re. U.S. Appl. No. 10/622,535, filed Jul. 21, 2003: Non Final Office Action mailed Feb. 6, 2009.

In the United States Patent and Trademark Office, in Re. U.S. Appl. No. 10/622,535, filed Jul. 21, 2003: Non Final Office Action mailed Jan. 31, 2008.

In the United States Patent and Trademark Office, in Re. U.S. Appl. No. 10/622,535, filed Jul. 21, 2003: Non Final Office Action mailed Nov. 8, 2006.

In the United States Patent and Trademark Office, in Re. U.S. Appl. No. 10/622,535, filed Jul. 21, 2003: Non Final Office Action mailed Sep. 12, 2007.

In the United States Patent and Trademark Office, in Re. U.S. Appl. No. 10/622,535, filed Jul. 21, 2003: Notice of Allowance mailed Jul. 20, 2009.

In the United States Patent and Trademark Office, in Re. U.S. Appl. No. 10/622,535, filed Jul. 21, 2003: Final Rejection mailed May 23, 2006.

In the United States Patent and Trademark Office, in Re. U.S. Appl. No. 10/622,535, filed Jul. 21, 2003: Notice of Allowance mailed Nov. 17, 2009.

In the United States Patent and Trademark Office, in Re. U.S. Appl. No. 11/512,327, filed Aug. 30, 2006: Notice of Allowance mailed Oct. 8, 2009.

In the United States Patent and Trademark Office, in Re. U.S. Appl. No. 11/512,327, filed Aug. 30, 2006, Final Rejection mailed Jun. 23, 2009.

In the United States Patent and Trademark Office, in Re. U.S. Appl. No. 11/512,327, filed Aug. 30, 2006, Non Final Rejection mailed Oct. 6, 2008.

International Patent Application No. PCT/US2005/33007: International Search Report dated Oct. 20, 2006, 1 page.

International Patent Application No. PCT/US2008/056960: International Search Report dated Jul. 28, 2008, 6 pages.

Kenna et al., "Design Rational for the Porous Coated Anatomic Total Knee System", Total Knee Arthroplasty, A Comprehensive Approach, 1984, 71-88.

Kenna et al., "Preliminary Experience with a Total Knee Prosthesis with Porous Coating Used without Cement", Clinical Orthopaedics and Related Research, Jun. 1983, 176, 95-107.

Marnay, "L'Arthroplastie Intervertebrale Lombaire", Chirurgien Orthopediste, Jun.-Sep. 1991, 25, 8 pages.

Marnay, "Lumbar Intervertebral Arthroplasty", Orthopedic Surgeon, Kennedy Clinic, No month or year available, 15 pages.

Plaintiff Spine Solutions Inc.'s Motion for Leave to File a Response to Defendants' Surreply Memorandum Regarding Plaintiff's Motion for Partial Summary Judgment of Failure of Defendants to State a Legal Defense or Claim for Relief Based on Inequitable Conduct and a Declaration of Marvin Petry in Support hereto, In the United States District Court, Western District of Tennessee, Case No. 2:07-cv-02175-JPM-dkv, filed Jun. 25, 2008, 2 pages.

Plaintiff Spine Solutions Inc.'s Opening Markman Brief, In the United States District Court, Western District of Tennessee, Case No. 2:07-cv-02175-JPM-dkv, filed Feb. 19, 2008, 26 pages.

Plaintiff Spine Solutions Inc.'s Reply Memorandum in Support of Motion for Partial Summary Judgment of Failure of Defendants to State a Legal Defense or Claim for Relief Based on Inequitable Conduct, In the United States District Court, Western District of Tennessee, Case No. 2:07-cv-02175-JPM-dkv, filed Mar. 31, 2008, 17 pages.

Szpalski et al., "Spine Athoplasty: A Historical Review", Eur. Spine J., Jun. 2002, 11(Suppl. 2), S65-S84.

Tooms, "Arthroplasty of Ankle and Knee", Campbell's Operative Orthopaedics, Seventh Ed., 1987, 2, 1145-1152.

Viscogliosi et al., "Spine Arthroplasty: Market Potential & Technology Update", Spine Industry Analysis Series, Nov. 2001, 202 pages.

* cited by examiner

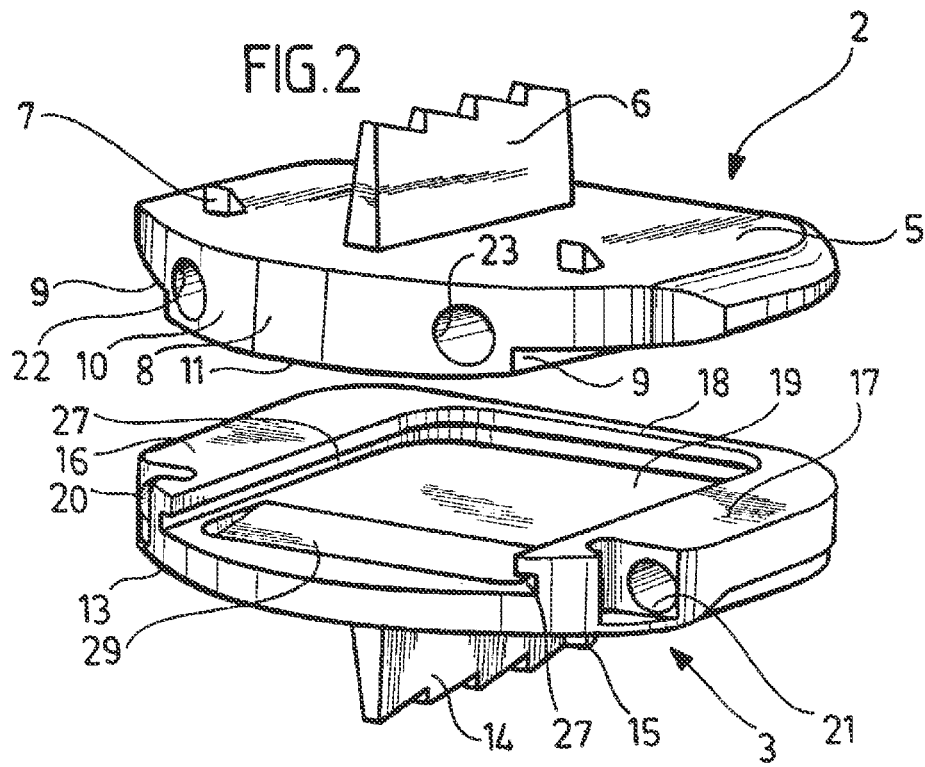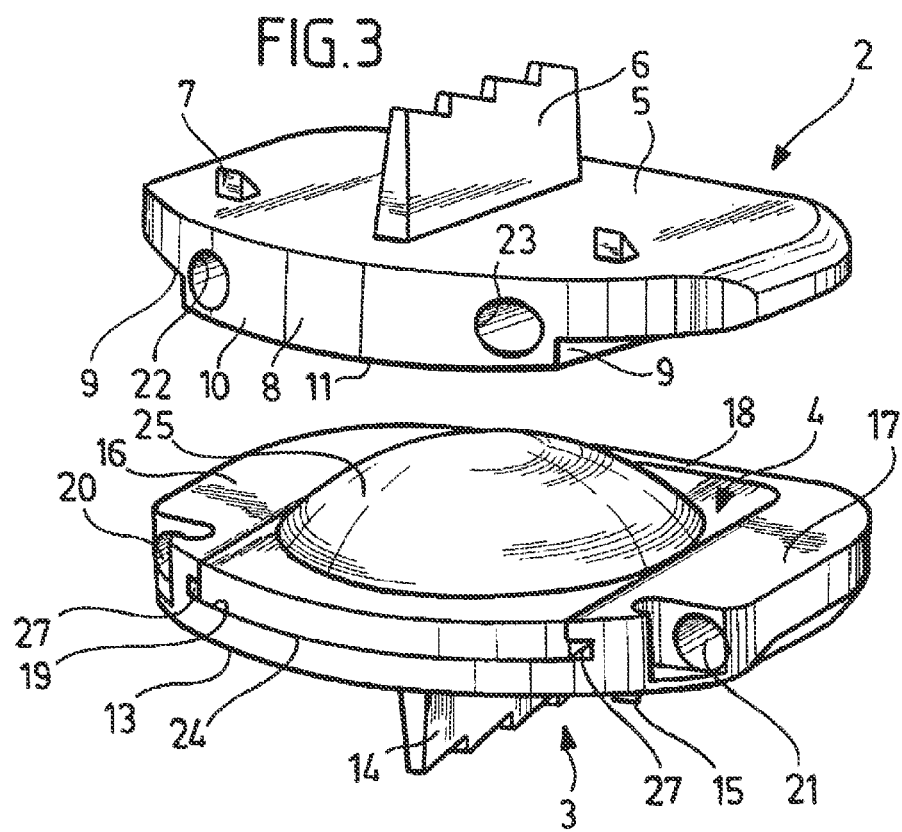

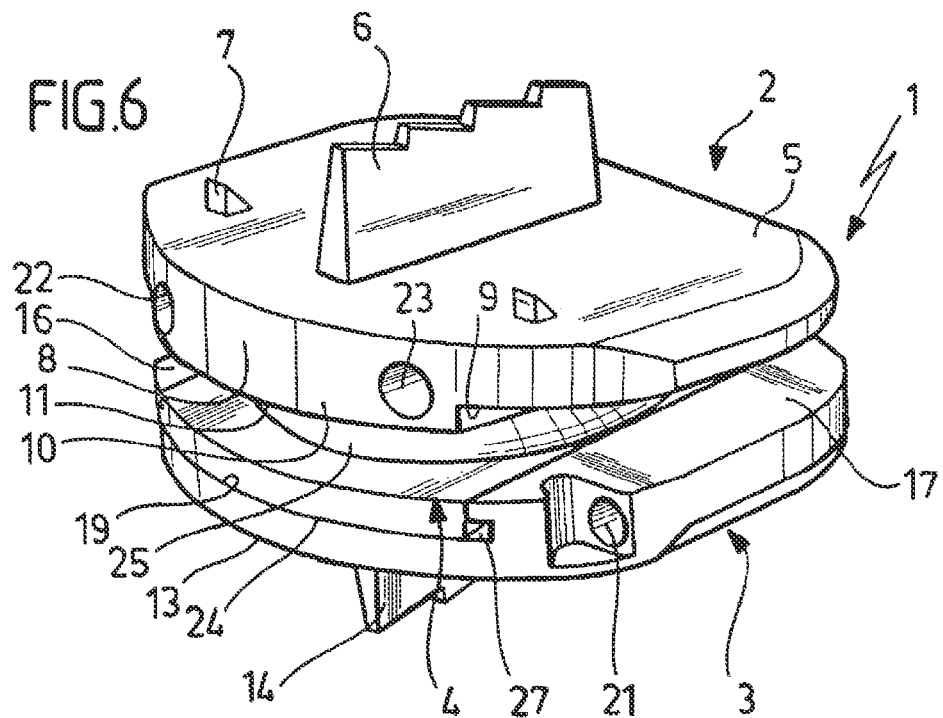
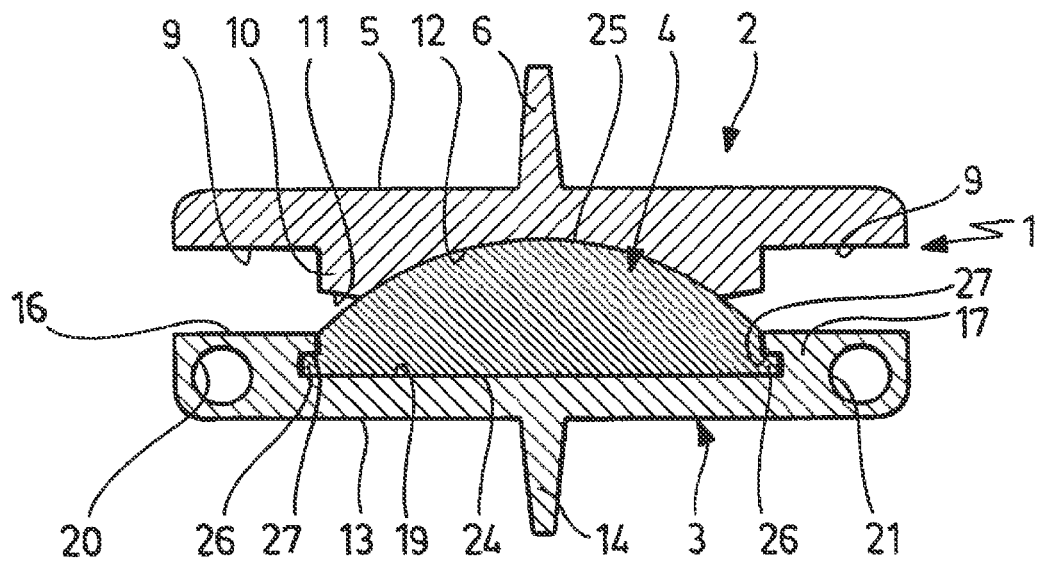

INTERVERTEBRAL IMPLANT

CROSS REFERENCE TO RELATED APPLICATIONS

This application is a continuation of U.S. application Ser. No. 10/998,951 filed Nov. 30, 2004, now U.S. Pat. No. 8,506,634, which is a continuation of application Ser. No. 10/018,402, filed Jun. 12, 2002, now U.S. Pat. No. 6,936,071, which is a national stage entry of PCT/EP99/04628 filed Jul. 2, 1999, the entire disclosures of which are incorporated herein by reference.

BACKGROUND

The invention relates to an intervertebral implant, having an upper part that has a support face for a vertebra and a lower part that has a support face for an adjacent vertebra, on each of which parts engagement elements, which are accessible from one side of the intervertebral implant, for a manipulation instrument are disposed, in order to minimize the structural height of the intervertebral implant upon insertion into an intervertebral space.

One such intervertebral implant is known for instance from U.S. Pat. No. 5,314,477. This intervertebral implant is used to replace a disk removed from the intervertebral space, and accordingly the intervertebral implant must have a relatively low structural height, since it has to fit into the gap between vertebrae. This is particularly difficult if an additional pivot insert is also embedded between the upper part and the lower part, as is the case in the known intervertebral implant of U.S. Pat. No. 5,314,477.

But even in two-piece intervertebral implants, difficulties also arise, especially if the implants also have pins and other protrusions on their support faces that are intended for anchoring the intervertebral implant in the bone. Often, these parts can be inserted only by widening the intervertebral space greatly. Not only is this difficult, but it also presents the risk of injuries.

Since the intervertebral space has a relatively low height, it is also difficult for engagement elements that a manipulation instrument can engage to be secured to both parts of the intervertebral implant. It is conventional to have such manipulation instruments engage the upper part and the lower part separately, for instance by means of pins that are inserted into bores on the upper part and lower part, so that with the manipulation instrument, the two parts of the intervertebral implant can be inserted into the intervertebral space and can optionally also be varied in terms of their spacing from one another, thereby allowing a certain spreading open of the intervertebral space. In this respect, reference is made to the pincerlike manipulation instrument of U.S. Pat. No. 5,314,477.

Because of the strong forces, it is necessary to provide a certain structural height for the engagement elements; for instance, the receiving bores must have a certain diameter. This dictates a minimum structural height for the upper part and for the lower part, and in conventional intervertebral implants, the structural heights of the upper part and lower part are thus added together, so that even if the upper and lower parts rest directly on one another, a relatively great structural height of the intervertebral implant is still unavoidable.

SUMMARY OF THE INVENTION

It is the object of the invention to embody an intervertebral implant of this generic type in such a way that the minimum structural height is reduced, to make it easier to insert the intervertebral implant into the intervertebral space.

In an intervertebral implant of the type described at the outset, this object is attained in accordance with the invention in that it is proposed that the upper part and lower part each have protrusions and recesses aimed at the respectively other part, which are offset laterally from one another in such a way that when the upper part has been brought close to the lower part they mesh with one another; and that the engagement elements on the upper part and on the lower part are each disposed in protrusions of these parts in such a way that the engagement elements of the upper part and lower part are located side by side and at least partly overlap in the direction of the height of the intervertebral implant.

In such an embodiment, a minimal structural height of the two intervertebral implant parts resting on one another can be attained, since the engagement elements, which cannot fall below a minimal structural height, are each disposed in protrusions of the upper part and lower part, or in other words in the parts of the upper part and lower part that have the greatest structural height. These regions of great structural height are embodied as protrusions, next to which are respective recesses, into which the protrusions of the respectively other part can dip. As a result, on the one hand, the engagement elements for the manipulation instruments are located side by side, and on the other, they can at least partly overlap, so that the total structural height of the parts resting on one another of the intervertebral implant can be reduced markedly compared to conventional intervertebral implants. The result is accordingly an interested arrangement of the upper and lower parts, with maximal exploitation of the available material height.

It is favorable if the engagement elements are insertion openings for pinlike retaining elements of a manipulation instrument; because of the described construction, these insertion openings can have a relatively large diameter and can thus receive strong retaining pins, and nevertheless a relatively low structural height of the intervertebral implant with parts resting directly on one another is obtained.

It is advantageous if the insertion openings extend substantially parallel to the support faces; once again, this prevents an increase in the structural height of the intervertebral implant parts.

In a preferred embodiment, it is provided that the lower part has a central indentation, opposite the lower support face, which indentation is surrounded by a U-shaped edge. Thus with the lower part and upper part resting directly on one another, the indentation serves to receive a protrusion on the upper part.

It is advantageous if the upper part has a central protrusion that fits substantially in complimentary fashion into the indentation; that is, the total volume of the indentation is utilized for the protrusion.

It is also advantageous if the engagement elements of the lower part are disposed on the two ends of the U-shaped edge, or in other words are located on the outside.

Conversely, the engagement elements of the upper part can be disposed on the central protrusion of the upper part, or in other words are located farther inward than the engagement elements of the upper part.

In particular, the engagement elements of the upper part can be disposed near the lateral edges of the central protrusion, so that for the upper part as well, the spacing of the engagement elements can be selected to be relatively great; as a result, both the upper part and the lower part can be reliably secured against skewing.

It should already be noted here that the words "lower part" and "upper part" do not necessarily say anything about the installed position of the intervertebral implant in the spinal column; the part called the "lower part" could in fact be above in the spinal column. What is essential is merely that the upper part and lower part define the intervertebral implant on opposite sides of the implant.

It is especially advantageous if the upper part and/or the lower part is embodied in substantially platelike fashion; these parts naturally, in accordance with the design of the invention, have protrusions and recesses that are oriented toward the respectively other part. The platelike embodiment, however, leads as a whole to a very low structural height of the intervertebral implant.

In a preferred embodiment, the lower part and the upper part each have a respective receptacle for a pivot insert. This pivot insert, which is placed between the upper part and lower part after the insertion of the intervertebral implant, supports the upper part and lower part against one another; it takes on a resilient function, for instance, and furthermore leads to a certain pivotability of the two parts of an intervertebral implant relative to one another, so that a pivotability of the adjacent vertebra is thus attainable as well.

In particular, it is advantageous if the pivot insert has at least one spherical support face, which engages the correspondingly spherically shaped receptacle.

It is favorable if the spherical receptacle is disposed in the central protrusion of the upper part.

It is also advantageous if the central indentation of the lower part forms the receptacle for the pivot insert.

According to a preferred embodiment of the invention, it is provided that the pivot insert can be inserted from the side into the receptacle, which has the engagement elements for a manipulation instrument. This is the side from which the upper part and lower part are introduced into the intervertebral space, and it is also from this side that the pivot insert can then be thrust between the already-inserted parts of the intervertebral implant.

It is favorable if the pivot insert is insertable into the receptacle along a guide.

In that the insert as well is preferably embodied substantially in platelike fashion.

An especially favorable design is obtained if the insert substantially completely fills up the central receptacle and with its spherical support face protrudes from the receptacle.

BRIEF DESCRIPTION OF THE DRAWINGS

The ensuing description of preferred embodiments of the invention serves in conjunction with the drawing to provide further explanation. Shown are:

FIG. 2: a perspective exploded view of the upper part and the lower part of the intervertebral implant, without an inserted pivot insert;

FIG. 3: a view similar to FIG. 2 with the pivot insert inserted into the lower part;

FIG. 6: a perspective view of the intervertebral implant with the pivot insert inserted; and FIG. 7: a cross-sectional view of the intervertebral implant of FIG. 6.

DETAILED DESCRIPTION OF ILLUSTRATIVE EMBODIMENTS

Figure 1:
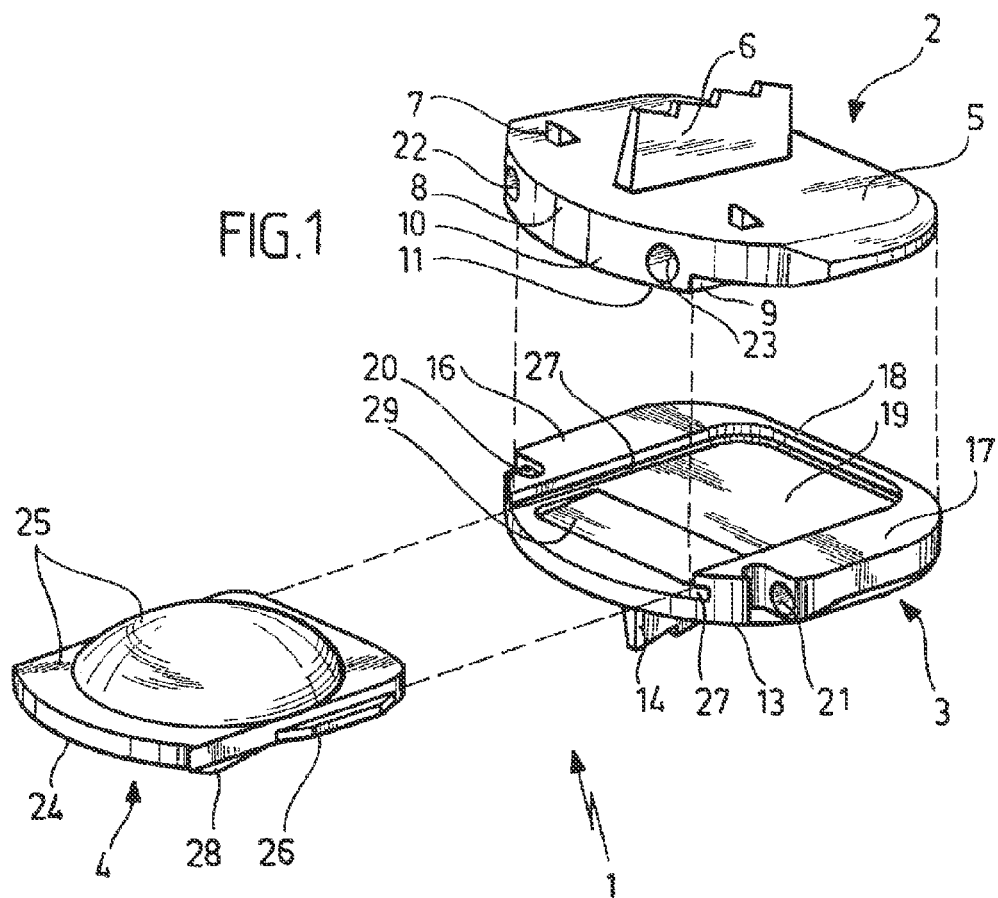
FIG. 1: a perspective exploded view of an intervertebral implant with an upper part, a lower part, and a pivot insert that can be inserted between them.

The intervertebral implant 1 shown in the drawing includes three parts, namely a platelike upper part 2, a platelike lower part 3, and a substantially platelike pivot insert 4.

The upper part 2 is embodied flat on its top, thus creating a support face 5, on which various kinds of protrusions 6, 7 are disposed which serve the purpose of anchoring the upper part 2 in a vertebra that rests, with its end face toward an intervertebral space, on the support face 5.

The upper part 2 is substantially rectangular in cross section; in the exemplary embodiment shown, a longitudinal edge 8 curves outward.

On the two short sides of this rectangle, the thickness of the platelike upper part 2 is less than in the central region, so that along the short sides of the upper part 2, downward-pointing recesses 9 each extending parallel to these edges are formed that are open toward the outside. The central region of the upper part 2 is located between the two recesses 9 and thus has a greater thickness or height and thus forms a downward-pointing protrusion 10 embodied between the two recesses 9. This protrusion is defined by an underside 11, which extends substantially parallel to the support face 5 and in which there is a spherical indentation 12, which forms a bearing plate for the pivot insert 4.

The lower part 3 of the intervertebral implant 1 is also platelike in embodiment and on its underside has a flat support face 13 with protrusions 14 and 15, which correspond to the protrusions 6 and 7 of the support face 5. On the side remote from the support face 13, the thickness of the lower part 3 is less in the central region than in an outer region. This outer region of greater thickness has the form of a U, with two parallel legs 16, 17, which extend parallel to the short edges of the lower part 3, which in cross section is embodied similarly to the upper part 2, and with a crosspiece 18 that connects the two legs 16 and 17 on one end. The region enclosed by the legs 16 and 17 and the crosspiece 18 forms a central indentation 19, whose area is substantially equivalent to the area of the central protrusion 10 of the upper part 2, while the disposition and length of the legs 16 and 17 correspond essentially to the disposition and length of the recesses 9 on the upper part 2. As a result, it is possible to place the upper 2 and lower part 3 on one another in such a way that the central protrusion 10 of the upper 2 dips into the central indentation 19, while the legs 16 and 17 of the lower part 3 dip into the recesses 9 of the upper part 2 (FIG. 4); in this position, the upper part 2 and lower part 3 have maximum proximity to one another and a minimal structural height.

The dimensions are selected such that the various recesses are essentially filled completely by the protrusions dipping into them.

Blind bores 20 and 21 are machined into the two legs 16 and 17 of the lower part 3, extending parallel to these legs 16, 17 from their free ends; the diameter of these bores is relatively great in proportion to the height of the legs 16, 17, and this diameter is in fact greater than the thickness or height of the lower part 3 in the region of the central indentation 19.

Blind bores 22 and 23, which extend parallel to the blind bores 20 and 21. in the lower part 3, are machined into the central protrusion 10 of the upper part 2, in the vicinity of its side edges. These blind bores 22 and 23 again have a relatively great diameter, which corresponds to a substantial portion of the height of the protrusion 10 and is greater than the thickness of the upper part 2 in the region of the recesses 9.

Figure 4:
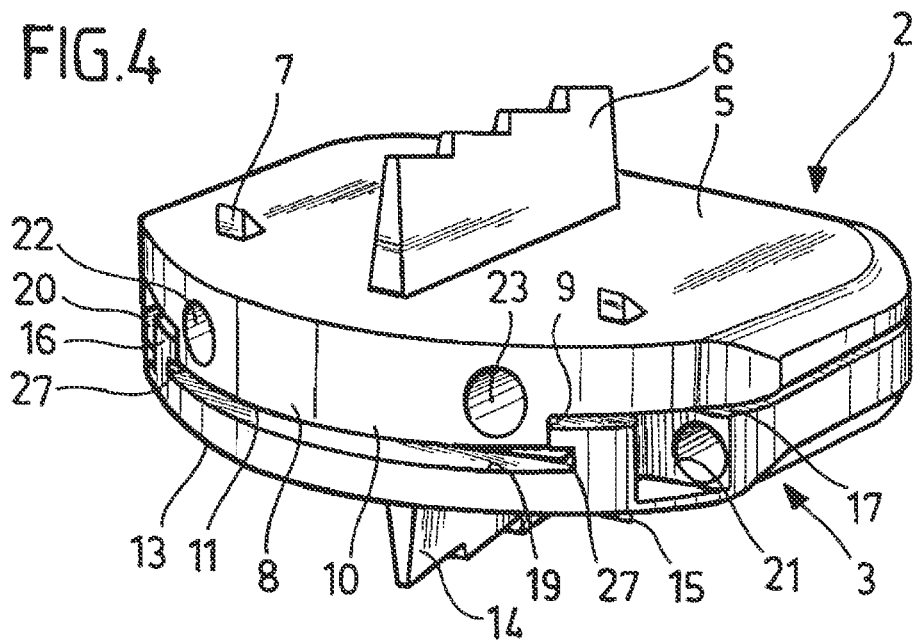
FIG. 4: a perspective view of the upper part and the lower part of the intervertebral implant with maximum mutual proximity.
Figure 5:
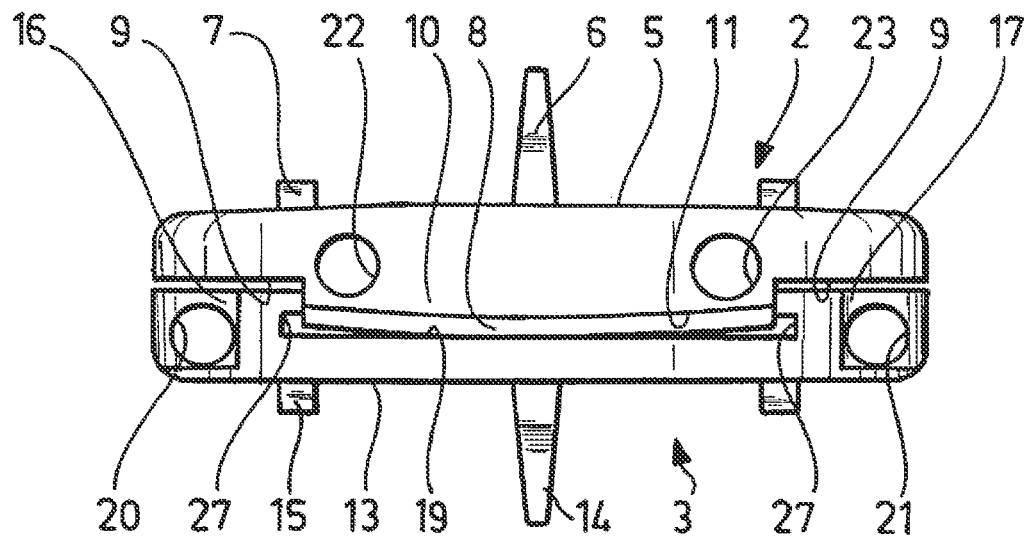
FIG. 5: a front view of the intervertebral implant of FIG. 4.

When the upper part 2 and lower part 3 rest tightly against one another in the manner described, the blind bores 20 and 21 of the lower part 3 and the blind bores 22 and 23 of the upper part 2 overlap at least partly in the direction of the height of the intervertebral implant 1, as is clearly shown in FIGS. 4 and 5.

The blind bores 20, 21, 22 and 23 serve as receptacles for pinlike extensions of a manipulation instrument, not shown in the drawing, and thus form engagement elements for this manipulation instrument, which in this way separately engages the upper part 2 and the lower part 3. With this manipulation instrument, it is possible to introduce the upper part 2 and the lower part 3 of the intervertebral implant 1 into an intervertebral space; the very low structural height of the intervertebral implant 1 facilitates this introduction, which can be done essentially without major widening of the intervertebral space.

After the introduction of the upper part 2 and lower part 3 in this way, the two parts of the intervertebral implant 1 can be spread apart; that is, their spacing is increased, for instance with the aid of the manipulation instrument that is holding the upper 2 and the lower part 3.

In this spread-open position of the upper part 2 and lower part 3, it is possible to thrust the pivot insert 4 between the upper part 2 and the lower part 3.

This pivot insert is constructed essentially in the shape of a plate, which has a flat underside 24. and a spherically upward-curved top side 25. The outer dimensions of the platelike pivot insert correspond to those of the central indentation 19 in the lower part 3, so that the pivot insert 4 can be thrust into this indentation, filling it up, specifically from the side toward which the blind bores 20, 21, 22, 23 open. Guide strips 26 on the side edges of the pivot insert 4 engage corresponding guide grooves 27 in the legs 16, 17, so that an insertion guide for the pivot insert 4 is formed that fixes it in the lower part 3 after its insertion. The inserted pivot insert 4, after insertion, fills up the indentation 19 and protrudes with its spherically curved top side 25 upward past the top side of the lower part 3; the spherical top side 25 dips in complimentary fashion into the spherically curved indentation 12 on the underside of the protrusion 10, wherewith the upper part 2 it forms a ball joint, which enables a certain pivotability of the upper part 2 relative to the lower part 3 (FIG. 7).

The pivot insert 4 can have a detent protrusion 28 on its flat underside 24; when the pivot insert 4 is inserted into the lower part 3, this protrusion locks elastically into a detent recess 29 that is located on the bottom of the indentation 19; as a result, the pivot insert 4 is also fixed in the insertion direction in the indentation 19.

The upper part 2 and lower part 3 are preferably made of physiologically safe metal, such as titanium, while the pivot insert 4 preferably comprises a likewise physiologically safe plastic material, such as polyethylene. These support faces 5 and 13 can be embodied in an especially bone-compatible way; for instance, this surface can be roughened by a coating, so that optimal anchoring to the adjacent bone material is obtained.

What is claimed:

1. An intervertebral implant sized and configured to replace a natural disk removed from an intervertebral space between opposing end faces of a first vertebra and an adjacent second vertebra, the intervertebral implant having a height extending in a first direction, a width extending in a second direction, and a depth extending in a third direction, where the first, second, and third directions are each perpendicular to each other, the implant having a maximum width greater than an implant maximum depth, the implant comprising:

a first part having an outer surface facing substantially in the first direction and configured to rest against the end face of the first vertebrae and having an inner surface facing substantially opposite the outer surface, the inner surface comprising a concave portion;

a second part having a outer surface facing substantially opposite the outer surface of the first part and configured to rest against the end face of the second vertebrae and an opposing inner surface facing substantially in the first direction;

a pivot insert located between the first and second parts, the insert having a top surface comprising a convex portion that is configured to pivotally engage the concave portion of the inner surface of the first part such that the first part can pivot relative to the second part, and the pivot insert having a bottom surface opposite the top surface; and a first anchor located on the outer surface of the first part, the first anchor having a height extending in the first direction, a width extending in the second direction, and a depth extending in the third direction, wherein the first anchor has a first anchor base connecting the first anchor to the outer surface of the first part and wherein the first anchor base has a first base depth that extends depthwise substantially along a first midline that extends in the third direction and that is located essentially midway across a width of the outer surface of the first part, and a first base width that extends in the second direction and is less than the first base depth, where the first anchor has a first center height measured from the outer surface of the first part at a first center position located at approximately a center of the first midline and the first anchor has a mid-anchor width measured at a location half of the first center height and wherein the first center height is greater than the mid-anchor width of the first anchor, and the first base depth is greater than the mid-anchor width of the first anchor, and wherein the first anchor has a first anchor top opposite the first anchor base having a first top width extending in the second direction less than the first base width;

a second anchor located on the outer surface of the second part, the second anchor having a height extending in the first direction, a width extending in the second direction, and a depth extending in the third direction, wherein the second anchor has a second anchor base connecting the second anchor to the outer surface of the second part and wherein the second anchor base has a second base depth that extends depthwise substantially along a second midline that extends in the third direction and that is located essentially midway across a width of the outer surface of the second part, and a second base width that extends in the second direction and is less than the second base depth, where the second anchor has a second center height measured from the outer surface of the second part at a second center position located at approximately a center of the second midline and the second anchor has a mid-anchor width measured at a location half of the second center height and wherein the second center height is greater than the mid-anchor width of the second anchor, and the second base depth is greater than the mid-anchor width of the second anchor, and wherein the second anchor has a second anchor top opposite the second anchor base having a second top width extending in the second direction less than the second base width;

wherein the first center height is greater than a height of a remainder of the first part measured from the outer surface of the first part to the inner surface of the first part at the first center position; and wherein the first midline is the only location on the outer surface of the first part having an anchor having a height equating to the first center height.

2. The intervertebral implant of claim 1 wherein the convex portion of the top surface of the insert is a spherical surface and wherein the insert comprises a sidewall that extends circumferentially around the insert and connects the top surface and the bottom surface of the insert and wherein the insert further comprises a substantially planar portion on the top surface that completely surrounds the spherical surface and is located between the spherical surface and the sidewall.

3. The intervertebral implant of claim 2 wherein the outer surface for both the first and second parts is substantially planar and comprises a roughened coating to augment anchoring the first and second parts to the adjacent first and second vertebrae.

4. The intervertebral implant of claim 3 wherein the inner surface of the second part comprises an indentation and the bottom surface of the pivot insert has a protrusion facing the indentation designed to fit within the indentation of the inner surface of the second part.

5. The intervertebral implant of claim 2 wherein the first and second anchors do not have screw holes designed and configured to retain a bone screw.

6. An intervertebral implant sized and configured to replace a natural disk removed from an intervertebral space between opposing end faces of a first vertebra and an adjacent second vertebra, the intervertebral implant having a height extending in a first direction, a width extending in a second direction, and a depth extending in a third direction, where the first, second, and third directions are each perpendicular to each other, the implant having a maximum width greater than an implant maximum depth, the implant comprising:

a first part having an outer surface facing substantially in the first direction and configured to rest against the end face of the first vertebrae and having an inner surface facing substantially opposite the outer surface, the inner surface comprising a concave portion;

a second part having an outer surface facing substantially opposite the outer surface of the first part and configured to rest against the end face of the second vertebrae and an opposing inner surface facing substantially in the first direction;

a pivot insert located between the first and second parts, the insert having a top surface comprising a convex portion that is configured to pivotally engage the concave portion of the inner surface of the first part such that the first part can pivot relative to the second part, and the pivot insert having a bottom surface opposite the top surface; and a first anchor located on the outer surface of the first part, the first anchor having a height extending in the first direction, a width extending in the second direction, and a depth extending in the third direction, wherein the first anchor has a first anchor base connecting the first anchor to the outer surface of the first part and wherein the first anchor base has a first base depth that extends depthwise substantially along a first midline that extends in the third direction and that is located essentially midway across a width of the outer surface of the first part, and a first base width that extends in the second direction and is less than the first base depth, where the first anchor has a first center height measured from the outer surface of the first part at a first center position located at approximately a center of the first midline and the first anchor has a mid-anchor width measured at a location half of the first center height and wherein the first center height is greater than the mid-anchor width of the first anchor, and the first base depth is greater than the mid-anchor width of the first anchor, and wherein the first anchor has a first anchor top surface opposite the first anchor base having a first top width extending in the second direction less than the first base width;

a second anchor located on the outer surface of the second part, the second anchor having a height extending in the first direction, a width extending in the second direction, and a depth extending in the third direction, wherein the second part anchor has a second anchor base connecting the second anchor to the outer surface of the second part and wherein the second anchor base has a second base depth that extends depthwise substantially along a second midline that extends in the third direction and that is located essentially midway across a width of the outer surface of the second part, and a second base width that extends in the second direction and is less than the second base depth, where the second anchor has a second center height measured from the outer surface of the second part at a second center position located at approximately a center of the second midline and the second anchor has a mid-anchor width measured at a location half of the second center height and wherein the second center height is greater than the mid-anchor width of the second anchor, and the second base depth is greater than the mid-anchor width of the second anchor, and wherein the second anchor has a second anchor top opposite the second anchor base having a second top width extending in the second direction less than the second base width.

7. The intervertebral implant of claim 6 wherein the convex portion of the top surface of the insert is a spherical surface and wherein the insert comprises a sidewall that extends circumferentially around the insert and connects the top surface and the bottom surface of the insert and wherein the insert further comprises a substantially planar portion on the top surface that completely surrounds the spherical surface and is located between the spherical surface and the sidewall.

8. The intervertebral implant of claim 7 wherein the first and second anchors do not have screw holes designed and configured to retain a bone screw.

9. The intervertebral implant of claim 7 wherein the outer surface for both the first and second parts is substantially planar and comprises a roughened coating to augment anchoring the first and second parts to the adjacent first and second vertebrae.

10. The intervertebral implant of claim 9 wherein the inner surface of the second part comprises an indentation and the bottom surface of the pivot insert has a protrusion facing the indentation designed to fit within the indentation of the inner surface of the second part.

11. An intervertebral implant sized and configured to replace a natural disk removed from an intervertebral space between opposing end faces of a first vertebra and an adjacent second vertebra, the intervertebral implant having a height extending in a first direction, a width extending in a second direction, and a depth extending in a third direction, where the first, second, and third directions are each perpendicular to each other, the implant having a maximum width greater than an implant maximum depth, the implant comprising:

a first part having an outer surface facing substantially in the first direction and configured to rest against the end face of the first vertebrae and having an inner surface facing substantially opposite the outer surface, the inner surface comprising a concave portion;

a second part having an outer surface facing substantially opposite the outer surface of the first part and configured to rest against the end face of the second vertebrae and an opposing inner surface facing substantially in the first direction, the inner surface of the second part comprising an indentation;

a pivot insert located between the first and second parts, the insert having a top surface comprising a convex portion that is configured to pivotally engage the concave portion of the inner surface of the first part such that the first part can pivot relative to the second part, and the pivot insert having a bottom surface opposite the top surface comprising a protrusion sized and configured to fit within the indentation of the second part; and a first anchor located on the outer surface of the first part, the first anchor having a height extending in the first direction, a width extending in the second direction, and a depth extending in the third direction, wherein the first anchor has a first anchor base connecting the first anchor to the outer surface of the first part and wherein the first anchor base has a first base depth that extends depthwise substantially along a first midline that extends in the third direction and that is located essentially midway across a width of the first part outer surface, and a first base width that extends in the second direction and is less than the first base depth, where the first anchor has a first center height measured from the outer surface of the first part at a first center position located at approximately a center of the first midline and the first anchor has a mid-anchor width measured at a location half of the first center height and wherein the first center height is greater than the mid-anchor width of the first anchor, and the first base depth is greater than the mid-anchor width of the first anchor, and wherein the first anchor has a first anchor top opposite the first anchor base having a first top width extending in the second direction less than the first base width;

a second anchor located on the outer surface of the second part, the second anchor having a height extending in the first direction, a width extending in the second direction, and a depth extending in the third direction, wherein the second anchor has a second anchor base connecting the second anchor to the outer surface of the second part and wherein the second anchor base has a second base depth that extends depthwise substantially along a second midline that extends in the third direction and that is located essentially midway across a width of the outer surface of the second part, and a second base width that extends in the second direction and is less than the second base depth, where the second anchor has a maximum height measured from the outer surface of the second part and the second anchor has a mid-anchor width measured at a location half of the second anchor maximum height and wherein the maximum height of the second anchor is greater than the mid-anchor width of the second anchor, and the second base depth is greater than the mid-anchor width of the second anchor, and wherein the second anchor has a second anchor top opposite the second anchor base having a second top width extending in the second direction less than the second base width;

wherein the first center height is greater than a height of a remainder of the first part measured from the outer surface of the first part to the inner surface of the first part at the first center position; and wherein the first midline is the only location on the outer surface of the first part having an anchor having a height equating to the first center height.

12. The intervertebral implant of claim 11 wherein the convex portion of the top surface of the insert is a spherical surface and wherein the insert comprises a sidewall that extends circumferentially around the insert and connects the top surface and the bottom surface of the insert and wherein the insert further comprises a substantially planar portion on the top surface that completely surrounds the spherical surface and is located between the spherical surface and the sidewall.

13. The intervertebral implant of claim 12 wherein the outer surface for both the first and second parts is substantially planar and comprises a roughened coating to augment anchoring the first and second parts to the adjacent first and second vertebrae.

14. The intervertebral implant of claim 13 wherein the first and second anchors do not have screw holes designed and configured to retain a bone screw.

15. An intervertebral implant sized and configured to replace a natural disk removed from an intervertebral space between opposing end faces of a first vertebra and an adjacent second vertebra, the intervertebral implant having a height extending in a first direction, a width extending in a second direction, and a depth extending in a third direction, where the first, second, and third directions are each perpendicular to each other, the implant having a maximum width greater than an implant maximum depth, the implant comprising:

a first part having an outer surface facing substantially in the first direction and configured to rest against the end face of the first vertebrae and having an inner surface facing substantially opposite the outer surface, the inner surface comprising a concave portion;

a second part having an outer surface facing substantially opposite the outer surface of the first part and configured to rest against the end face of the second vertebrae and an opposing inner surface facing substantially in the first direction;

a pivot insert located between the first and second parts, the insert having a top surface comprising a convex portion that is configured to pivotally engage the concave portion of the inner surface of the first part such that the first part can pivot relative to the second part, and the pivot insert having a bottom surface opposite the top surface; and a first anchor located on the outer surface of the first part, the first anchor having a height extending in the first direction, a width extending in the second direction, and a depth extending in the third direction, wherein the first anchor has a first anchor base connecting the first anchor to the outer surface of the first part and wherein the first anchor base has a first base depth that extends depthwise substantially along a first midline that extends in the third direction and that is located essentially midway across a width of the outer surface of the first part, and a first base width that extends in the second direction and is less than the first base depth, where the first anchor has a first center height measured from the outer surface of the first part at a first center position located at approximately a center of the first midline and the first anchor has a mid-anchor width measured at a location half of the first center height and wherein the first center height is greater than the mid-anchor width of the first anchor, and the first base depth is greater than the mid-anchor width of the first anchor, and wherein the first anchor has a first anchor top opposite the first anchor base having a first top width extending in the second direction less than the first base width;

a second anchor located on the outer surface of the second part, the second anchor having a height extending in the first direction, a width extending in the second direction, and a depth extending in the third direction, wherein the second anchor has a second anchor base connecting the second anchor to the outer surface of the second part and wherein the second anchor base has a second base depth that extends depthwise substantially along a second midline that extends in the third direction and that is located essentially midway across a width of the outer surface of the second part, and a second base width that extends in the second direction and is less than the second base depth, where the second anchor has a maximum height measured from the outer surface of the second part and the second anchor has a mid-anchor width measured at a location half of the second anchor maximum height and wherein the maximum height of the second anchor is greater than the mid-anchor width of the second anchor, and the second base depth is greater than the mid-anchor width of the second anchor, and wherein the second anchor has a second anchor top opposite the second anchor base having a second top width extending in the second direction less than the second base width;

wherein the first center height is greater than a height of a remainder of the first part measured from the outer surface to the inner surface of the first part at the first center position; and wherein the first midline is the only location on the outer surface of the first part having an anchor having a height equating to the first center height.

16. The intervertebral implant of claim 15 wherein the convex portion of the top surface of the insert is a spherical surface and wherein the insert comprises a sidewall that extends circumferentially around the insert and connects the top surface and the bottom surface of the insert and wherein the insert further comprises a substantially planar portion on the top surface that completely surrounds the spherical surface and is located between the spherical surface and the sidewall.

17. The intervertebral implant of claim 16 wherein the outer surface for both the first and second parts is substantially planar and comprises a roughened coating to augment anchoring the first and second parts to the adjacent first and second vertebrae.

18. The intervertebral implant of claim 17 wherein the first and second anchors do not have screw holes designed and configured to retain a bone screw.

* * * * *